United States Patent [19]

Berg

[11] 4,240,978
[45] Dec. 23, 1980

[54] PROCESS FOR SULFONATION OF GAS OILS

[75] Inventor: Roy C. Berg, Park Ridge, Ill.

[73] Assignee: UOP Inc., Des Plaines, Ill.

[21] Appl. No.: 101,296

[22] Filed: Dec. 7, 1979

[51] Int. Cl.$^3$ .............................................. C07C 143/24
[52] U.S. Cl. .............................. 260/505 P; 260/505 R
[58] Field of Search .......................... 260/505 P, 505 R

[56] References Cited

U.S. PATENT DOCUMENTS

| 2,680,716 | 6/1954 | Lipkin et al. | 252/33 |
|---|---|---|---|
| 3,050,464 | 8/1962 | Brown et al. | 252/33 |
| 3,302,713 | 2/1967 | Ahearn et al. | 166/9 |
| 3,803,088 | 4/1974 | Marty | 260/505 |
| 4,144,266 | 3/1979 | Plummer et al. | 260/505 |

*Primary Examiner*—Alan Siegel
*Attorney, Agent, or Firm*—James R. Hoatson, Jr.; John F. Spears, Jr.; William H. Page, II

[57] ABSTRACT

A process for the production of oil-soluble sulfonates from a gas oil such as a vacuum gas oil. Water-soluble sulfonic acids are separated from the effluent of the sulfonation zone, and the remainder of the effluent is then passed through a saponification zone to produce oil-soluble sulfonates which are then recovered. The remaining hydrocarbons are fractionated, with the resultant heavy fraction being passed through a reforming zone to produce additional aromatics which are then recycled to the sulfonation zone.

6 Claims, 1 Drawing Figure

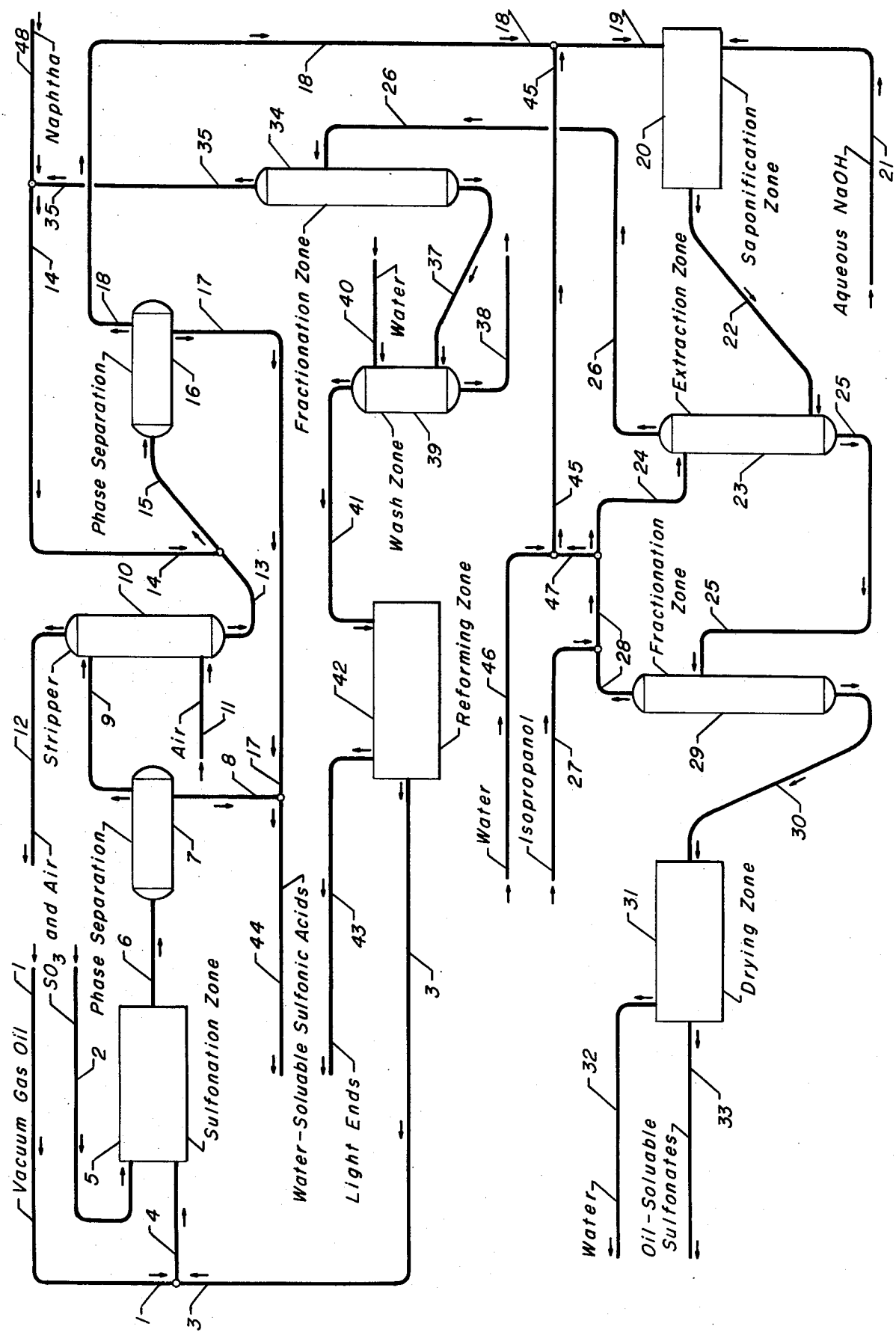

PROCESS FOR SULFONATION OF GAS OILS

FIELD OF THE INVENTION

The invention relates to a hydrocarbon conversion process. The invention more specifically relates to a process for sulfonation of aromatic hydrocarbons. The invention is particularly directed to a process for producing oil-soluble petroleum sulfonates which may be used in enhanced oil recovery methods by the sulfonation of a vacuum gas oil. References concerned with these processes may be found in U.S. patents classified in Classes 252 and 260, with many references being concentrated in Class 260–505.

PRIOR ART

The large amount of crude oil which may be recovered only by the application of advanced oil recovery techniques has prompted a large amount of research in this area. Examples of oil recovery processes using surfactants are presented in U.S. Pat. Nos. 3,994,342; 4,120,358; 4,124,512 and 4,147,638. U.S. Pat. No. 3,302,713 is a similar reference which is relevant for its teaching of the direct sulfonation of a vacuum gas oil, with surfactants being produced by the subsequent neutralization (saponification) of the sulfonates. U.S. Pat. No. 4,144,266 (Cl. 260–505S) teaches the production of petroleum sulfonates from crude oils and topped crude oils and discloses the recycling of unreacted hydrocarbons to the sulfonation zone.

U.S. Pat. No. 2,680,716 (Cl. 252–33) is relevant for its teaching of the various steps which may be performed in a process for the production of petroleum sulfonates. These steps included the separation and saponification of the oil-soluble sulfonic acids and the extraction of the resultant sulfonates to yield a raffinate which can be recycled to the sulfonation zone.

Processes for reforming petroleum-derived hydrocarbons are well described in available references, such as the article starting at page 2 of *Industrial Engineering and Chemistry*, Prod. Res. Dev., Vol. 15, No. 1, 1976. U.S. Pat. No. 3,050,464 is relevant for its teaching of a process for reforming a lubricating oil boiling range stock to increase the possible yield of oil-soluble sulfonates produced from the lubricating oil.

SUMMARY OF INVENTION

The invention provides a process for converting a vacuum gas oil into water-soluble sulfonic acids and oil-soluble sulfonates. By the internal recycling and conversion of paraffinic hydrocarbons, a much higher yield of oil-soluble sulfonates is obtained than by prior art methods. One embodiment of the process may be characterized as a process for the production of petroleum sulfonates useful in crude oil production which comprises the steps of passing a feed stream comprising a mixture of aromatic and paraffinic hydrocarbonaceous compounds having a molecular weight between about 250 to about 450, $SO_3$, and a hereinafter specified recycle stream into a sulfonation zone maintained at sulfonation conditions and effecting the sulfonation of at least a portion of said aromatic hydrocarbonaceous compounds present in the feed stream, and thereby forming a sulfonation zone effluent stream which comprises the remaining unreacted paraffinic compounds, water-soluble sulfonic acids and oil-soluble sulfonic acids; separating water-soluble sulfonic acids from the sulfonation zone effluent stream; admixing a hydrocarbon stream comprising light hydrocarbons having boiling points within the naphtha boiling point range with the remaining second portion of the sulfonation zone effluent stream and separating the resultant admixture into a denser phase comprising water-soluble sulfonic acids and a less dense phase comprising oil-soluble sulfonic acids, the light hydrocarbon and said unconverted paraffinic hydrocarbons; passing a stream of the less dense phase through a saponification zone to thereby form a saponification zone effluent stream comprising the light hydrocarbons, said unconverted paraffinic hydrocarbon and oil-soluble petroleum sulfonates; extracting the oil-soluble sulfonates from the saponification zone effluent stream with an aqueous solution of an alkyl alcohol to thereby form an extract stream comprising oil-soluble sulfonates and a raffinate stream comprising the light hydrocarbons and said unconverted paraffinic hydrocarbons; recovering the oil-soluble sulfonates from the extract stream as a product; fractionating the raffinate stream into a light fraction comprising the light hydrocarbon and a heavy fraction comprising said unconverted paraffinic hydrocarbons; admixing the light fraction with the second portion of the sulfonation zone effluent as at least a portion of the previously referred to hydrocarbon stream; passing the heavy fraction through a reforming zone to effect the conversion of at least a portion of said unreacted paraffinic hydrocarbon into aromatic hydrocarbons and forming a reforming zone effluent stream; and passing the reforming zone effluent stream into the sulfonation zone as the previously referred to recycle stream.

DESCRIPTION OF THE DRAWING

The Drawing illustrates the preferred embodiment of the invention.

A stream of a vacuum gas oil flowing through line 1 is admixed with a recycle stream from line 3 and passed into a sulfonation zone 5 through line 4. Also passed into the sulfonation zone is a vapor phase stream comprising a mixture of $SO_3$ and air from line 2. A sizable percentage of the aromatic hydrocarbons present in the vacuum gas oil and the recycle stream are sulfonated within the sulfonation zone 5, and there is thereby produced a sulfonation zone effluent stream which comprises the unconverted paraffinic compounds present in the vacuum gas oil feed stream and the recycle stream, the residual $SO_3$, air and a mixture of mono- and disulfonated aromatic hydrocarbons. The sulfonation zone effluent stream is passed into a phase separation zone 7 through line 6. The denser water-soluble sulfonic acids settle from the sulfonation zone effluent stream and are removed through line 8. The remainder of the sulfonation zone effluent stream is passed through line 9 into a stripping column 10. A stream of air passed into the bottom of the stripping column through line 11 removes the residual $SO_3$ contained in the material entering the top of the stripping column. A vapor phase stream comprising the residual $SO_3$ and air is removed from the stripping column in line 12 and may be recycled in part to the sulfonation zone.

The stripped liquid which is removed from the bottom of the stripping column 10 is carried by line 13 and is admixed with a naphtha stream carried by line 14. The resultant admixture flows through line 15 and a mixing means not shown, such as an in-line mixer, into a second phase separation zone 16. The admixture of the naphtha into the material flowing through line 13 causes an additional amount of water-soluble sulfonic acids to drop out of solution as a denser phase which is collected in the phase separation zone. A stream of this denser phase material is removed through line 17 and combined with the liquid from line 8 to produce a first product stream of water-soluble sulfonic acids carried by line 44.

The less dense phase which forms in the second phase separation zone 16 is removed through line 18 and contacted with an isopropanol-water mixture from line 45 and then passed through line 19 into a saponification zone 20. The stream in line 19 comprises the great majority of the naphtha from line 14, the unconverted paraffinic hydrocarbons passed into the sulfonation zone, and the monosulfonated aromatic hydrocarbons produced in the sulfonation zone. The liquid from line 19 is admixed with an aqueous stream of sodium hydroxide from line 21 to effect the neutralization of the oil-soluble sulfonic acids and the production of oil-soluble sulfonates. A saponification zone effluent stream which comprises both the entering naphtha and unconverted paraffinic hycdrocarbons and also the oil-soluble sulfonates is passed into an extraction zone 23 through line 22.

The liquid mixture entering the bottom of the extraction zone 23 is contacted with a descending liquid phase comprising an aqueous solution of isopropanol fed to the extraction zone through line 24. The oil-soluble sulfonates are solubilized in the isopropanol solution to form an extract stream which is removed from the extraction zone through line 25 and passed into a fractionation zone 29. Fractionation zone 29 is preferably a single column which separates the extract stream into a bottom stream comprising the oil-soluble sulfonates removed in line 30 and an overhead stream comprising the isopropanol removed in line 28. The overhead stream of the fractionation zone is combined with makeup isopropanol from line 27 to form the solvent stream passed into the extraction zone through line 24. A portion of this isopropanol carried by line 47 is admixed with water from line 46 to form an isopropanol-water mixture which flows through line 45 to the saponification zone. The bottoms stream of the fractionation zone is passed into a drying zone 31. Water which is separated from the bottoms stream is removed through line 32 and a second product stream comprising the oil-soluble sulfonates is removed from the process through line 33.

A raffinate stream comprising the unreacted paraffinic hydrocarbons and the remaining naphtha is removed from the extraction zone 23 in line 26 and passed into a second fractionation zone 34. This fractionation zone is also preferably a single trayed column which separates the entering material into a naphtha fraction removed through line 35 and a heavy paraffinic fraction removed through line 37. The naphtha fraction is recycled by passage into the second phase separation zone and may be replenished by makeup naphtha from line 48. The heavy fraction is water-washed in wash zone 39 by countercurrent passage against a water stream flowing through lines 40 and 38. This removes a residual amount of sulfonates and other compounds which may be detrimental to the operation of the reforming zone 42. The heavy paraffinic fraction is passed into the reforming zone through line 41.

The reforming zone comprises both a reactor and a separation facility. Within the reforming zone, at least a portion of the paraffinic hydrocarbons which pass through the sulfonation zone without being sulfonated are converted into aromatic hydrocarbons and other olefinic hydrocarbons. The hydrogen and a small amount of light hydrocarbons which are produced incidental to the reforming operation are removed through line 43. There is thereby produced a reforming zone effluent stream which comprises aromatic hydrocarbons and which has a boiling point range similar to that of the vacuum gas oil of line 1. The reforming zone effluent stream is then passed into the sulfonation zone to effect the sulfonation of the just-produced aromatic hydrocarbons. In this manner, the entering vacuum gas oil may be recycled virtually to extinction and a very high yield of water-soluble sulfonic acids and oil-soluble sulfonates is obtained. This description of the preferred embodiment of the invention is not intended to preclude from the scope of the inventive concept those other embodiments set out herein or which are the result of normal and reasonable modifications of those embodiments.

DETAILED DESCRIPTION

Extremely large volumes of low cost surfactants will be needed in large scale tertiary oil recovery processes subsequent to secondary recovery processes such as waterflooding. The type of surfactants which will be in greatest demand are the oil-soluble surfactants, such as the monosulfonates of aromatic hydrocarbons. The availability of these preferred surfactants may be limited by the limited amount of aromatic hydrocarbons present in the feedstocks.

It is an objective of the subject invention to provide a process for the production of oil-soluble petroleum sulfonates. It is a further objective to increase the amount and ratio of such sulfonates which may be produced from a given gas oil feed stream.

The feed stream to the subject process is a gas oil produced by the fractionation of a crude oil or a reduced crude oil. The hydrocarbons and other hydrocarbonaceous compounds which are present in the feed preferably have a molecular weight of between about 250 to about 450. Some of the compounds present in the feed stream may have molecular weights outside this range. The compounds present in the feed stream will have a wide variety of structures as is typical of petroleum fractions and will contain aromatic, paraffinic and acyclic olefinic hydrocarbons. The relative concentration of each type of hydrocarbon will vary with the source of the crude oil. The aromatics concentration may reach 40 mol.% but is normally less than 30 mol.%. In a highly paraffinic crude oil, the aromatics concentration may be as low as 6 mol.%. One advantage of the subject process is that it allows the production of large quantities of aromatic sulfonates from such highly paraffinic crude oils, thereby making feasible the use of the recovered crude oil as the source of the surfactant used in its production.

The feed stream to the process is passed into a sulfonation zone in admixture with vaporous $SO_3$ and a recycle stream which is the net effluent of a reforming zone. Preferably, the $SO_3$ is substantially free of impurities such as $H_2SO_4$ and is anhydrous. From 5 to 30 lbs. of $SO_3$ may be passed into the sulfonation zone for every 100 lbs. of the feed stream. Preferably, only a slight excess of $SO_3$ above its rate of consumption is charged to the sulfonation zone. The $SO_3$ is preferably admixed with air prior to passage into the sulfonation zone. The reactor or reactors used within the sulfonation zone may be of any suitable type including falling film reactors, stirred tank reactors and tubular reactors. The sulfonation conditions maintained in the reactor preferably include a mildly superatmospheric pressure less than about 10 atmospheres and a temperature between about 15 and 150° C. Sulfonation conditions which tend to promote the production of monosulfonated hydrocarbons are preferred. The use of relatively low temperatures and low $SO_3$ concentrations are therefore preferred. Further details on the operation of sulfonation zones may be obtained from available references including U.S. Pat. No. 4,036,875 (Cl. 260–505S).

The effluent of the sulfonation zone will contain the products of the sulfonation reaction, the unreacted hydrocarbons originally present in the feed and recycle streams and any residual $SO_3$. Air or other gases charged to the sulfonation zone will also be present in this effluent stream. The main products of the sulfonation reaction are sulfonic acids. A sulfonic acid having two or more $SO_3$ groups per molecule is normally more water-soluble than the corresponding monosulfonated acid. Lower molecular weight hydrocarbons also tend to produce water-soluble sulfonic acids. As it is desired to maximize the production of oil-soluble sulfonates, the preferred sulfonic acids are of higher molecular weight mono-substituted sulfonic acids.

The effluent of the sulfonation zone is passed into the first of two phase separation zones which are used in the subject process. In the first separation zone, the sulfonation zone effluent stream is separated into two liquid phases and a vapor phase. The denser liquid phase comprises the water-soluble sulfonic acids which are often referred to as "green acids" in the older prior art references. Although it is desired to maximize the production of the oil-soluble sulfonates, the water-soluble sulfonic acids produced in the subject process also have the utility in that they may be employed in a crude oil recovery process as a sacrificial surfactant which remains attached to the oil-bearing rock.

Both the first and the second phase separation zones preferably comprise rather lengthy horizontal vessels having a sufficient volume to insure laminar flow of their contents. The phase separation zones are designed to be of a sufficient volume to allow the different liquid and vapor phases to accumulate as distinct layers within a separation vessel to thereby facilitate the separation of the different compounds by decantation. The less dense phase which is formed in the first phase separation zone, together with any vapors present in this zone, is removed from the phase separation zone and passed into a stripping zone. This zone preferably comprises a vertical trayed column wherein the entering liquid phase passes downward countercurrent to a rising air stream. An off-gas stream comprising the air and $SO_3$ which has been stripped from the liquid is removed from the top of the stripping column. This off-gas stream may be ejected directly to suitable off-gas treating facilities, but it is preferred that to the maximum extent feasible this off-gas stream is internally recycled as at least a portion of the $SO_3$-containing vapor stream passed into the sulfonation zone.

The liquid phase net effluent of the stripping zone is admixed with a stream of liquid phase naphtha boiling range hydrocarbon. This admixture may be performed in a stirred mixing tank or an in-line mixing device may be utilized. It is preferred that the naphtha boiling range or light hydrocarbons are added at a rate of from about 20 to 40% of the flow rate of the remainder of the sulfonation zone effluent stream. The resultant admixture is then passed into the second phase separation zone used in the subject process. The quiescent conditions maintained within this separation zone allow the separation by decantation of the additional amount of water-soluble sulfonic acids which drop out of solution because of the addition of the light hydrocarbons. The temperature maintained within the second phase separation zone and the rate of addition of the light hydrocarbons should be adjusted to minimize the solubility of the water-soluble sulfonic acids in the less dense phase which is formed in the separation zone.

The rate at which the light hydrocarbons are added to the remainder of the sulfonation zone effluent stream must be balanced against the cost increase of internally recycling higher amounts of the light hydrocarbons. The light hydrocarbons are gradually lost, as by dissolution in the water-soluble sulfonic acids withdrawn from the second separation zone, and the inventory of light hydrocarbons within the process must be continually supplemented by a small make-up stream of naphtha. The pressure maintained within the second phase separation zone should be a superatmospheric pressure above 0.5 atmospheres gauge which is sufficient to maintain liquid phase conditions. The temperature maintained within this zone is preferably within the broad range of from about 15° to 195° C.

A stream of the less dense phase which forms in the second separation zone is withdrawn and preferably mixed with a mixture of isopropanol and water, such as 50/50 vol.%, at a rate of from about 5 to 15 vol.% of the flow rate from the second separation zone and then passed into a saponification zone. A stirred tank reactor or a tubular reactor may be employed within this zone. The pressure maintained within the saponification zone should be sufficient to maintain the reactants in the liquid phase. A pressure below 15 atmospheres is preferred. The saponification conditions will also preferably include a temperature within the range of from about 15°–160° C. Temperatures and pressures outside of these ranges may be employed if desired. Also passed into the saponification zone is an aqueous stream of a strong alkaline solution such as sodium hydroxide or potassium hydroxide, with sodium hydroxide being preferred. The alkaline compound neutralizes the oil-soluble sulfonic acid to produce oil-soluble sulfonates which are predominately sodium alkylaromatic monosulfonate salts.

The hydrocarbons which were not sulfonated in the sulfonation zone and the light hydrocarbons which are employed to increase the removal of the water-soluble sulfonic acids are also present in the stream passed into the saponification zone and are substantially unaffected by the reactions which occur in the saponification zone. The effluent stream of the saponification zone therefore comprises a mixture of the unreacted high boiling point hydrocarbon, the naphtha boiling range hydrocarbon, the oil-soluble sulfonates produced in the saponification zone and a small amount of water from the alkaline solution.

The effluent of the saponification zone is passed into an extraction zone and is therein contacted with an aqueous solution of an alkylalcohol. Preferably, this alcohol has less than 5 carbon atoms per molecule. Isopropanol is the preferred alcohol. The aqueous solution used as the solvent stream preferably contains from about 25 to 60 wt.% alcohol. A batch-type extraction operation may be employed. However, it is greatly preferred that a continuous extraction operation is performed utilizing a single vertical trayed extraction column. The conditions employed within the extraction zone preferably include a pressure below about 15 atmospheres and a temperature below about 80° C. Conditions outside of these ranges may be employed if desired, with the pressure at all times being sufficient to maintain liquid phase conditions.

The oil-soluble sulfonates present in the effluent of the saponification zone dissolve in the isopropanol stream to form an extract stream which is removed from the extraction zone and is passed into a fractionation zone used to separate the sulfonates from the solvent material. This fractionation zone is preferably a single trayed column operated at a positive pressure and at a temperature above 100° C. This separation is not difficult due to the relatively major differences in volatility between the isopropanol and the oil-soluble sulfonates. The net overhead stream of the fractionation zone will contain the alcohol and water. The net bottoms stream of the fractionation zone will contain the oil-soluble sulfonates and some dissolved water. The net bottoms stream of the fractionation zone may be suitable for use in a water-flooding process. However, it is preferred that an additional amount of water is removed from the bottoms stream by the passage of the bottoms stream into a drying zone. In this drying zone, the net bottoms stream is subjected to an elevated temperature and a reduced pressure which promotes the vaporization of the more volatile water.

The unreacted gas oil boiling range hydrocarbons and the light naphtha boiling range hydrocarbons will pass through the extraction zone and are removed as a raffinate stream. This stream is passed into a second fractionation zone, which also preferably comprises a single vertical trayed fractionation column. This stream is basically a mixture of hydrocarbons and it is the function of this second fractionation zone to split this hydrocarbon mixture into a lighter naphtha fraction which is suitable for admixture with the sulfonation zone effluent stream and a heavier fraction which is to be recycled to the sulfonation zone. The net bottoms stream removed from the second fractionation zone is water-washed to remove any residual caustic, $SO_3$, or sulfonates which may be present. This water-washing step may be performed in one or more stirred tanks or a countercurrent water-hydrocarbon contacting apparatus may be employed.

The washed heavy hydrocarbon fraction produced in the second fractionation zone is passed into a reforming zone. This reforming zone includes the customary indirect heat exchange means, heater, reactor, reactor effluent separation equipment and a reactor effluent liquid stripping column. The reactor employed within the reforming zone may be a fixed bed reactor. Preferably, the reactor is of the moving-bed type having radial flow of the reactants through two or more beds of catalyst. The catalyst employed within the reforming zone preferably comprises from about 0.1 to about 1 wt.% of a Group VIII noble metal such as platinum, palladium, rhodium or iridium and from about 0.1 to about 5 wt.% of a combined halogen such as chlorine or fluorine. Platinum is the preferred Group VIII metal. The metal and the halogen component are preferably carried on a refractory inorganic support such as alumina spheres having diameters between 1/16 and ⅛ inch. The preferred reforming catalyst also contains tin and an alkali metal which is preferably lithium. Further details on the preferred type of reforming catalyst may be obtained from U.S. Pat. Nos. 3,531,543; 3,631,215 and 3,864,284.

The hydrocarbons are preferably passed through the reforming reactor while the reactor is maintained at reforming conditions which include a temperature of from about 290° C. to about 600° C., and preferably from about 370° C. to about 485° C. The vapor phase reforming reaction is normally performed in the presence of added hydrogen. A typical hydrogen to hydrocarbon mole ratio is 10:1 with a fixed bed operation, but may vary from about 0.5:1 to about 20:1. With a moving bed reactor, the catalyst is frequently regenerated and a lower hydrogen to hydrocarbon ratio of from about 1:1 to about 5:1 may be employed. Reforming conditions include a pressure of from about 25 to 1,000 psig. or higher, but the pressure is preferably kept within the range of 50 to about 200 psig. The liquid hourly space velocity of the reactants is normally within the range of from 0.5 to 10, with liquid hourly space velocities of from 1.0 to 5.0 being preferred. Further details on the reforming of hydrocarbons may be obtained by reference to U.S. Pat. Nos. 3,050,464; 3,647,680; 3,821,104; 3,650,944; 3,830,727; and 3,647,679.

The effluent of the reforming reactor is cooled to effect a partial condensation and is then separated into a liquid phase containing the very great majority of the $C_6$-plus hydrocarbons and a vapor phase which is rich in hydrogen. At least a portion of the vapor phase is preferably recycled for use in the reactor. The liquid phase is passed into a stripping column which is operated at conditions effective to remove from the entering material all hydrocarbons which are lighter than the lightest hydrocarbons present in the feed stream. The net bottoms stream of the stripping column is preferably a mixture of olefinic and aromatic hydrocarbons which has a boiling point range similar to the feed stream. Preferably, at least the majority of the aromatic hydrocarbons present in this stream are formed within the reforming zone from paraffinic hydrocarbons which had previously passed through the sulfonation zone. The bottoms stream of the stripping column is referred to herein as the reforming zone effluent stream and is passed into the sulfonation zone in admixture with the feed stream.

One embodiment of the invention may be characterized as a process for the production of petroleum sulfonates useful in crude oil production which comprises the steps of passing a feed stream comprising a mixture of aromatic and paraffinic hydrocarbonaceous compounds having a molecular weight between about 250 and about 450, $SO_3$, and a hereinafter specified recycle stream into a sulfonation zone maintained at sulfonation conditions and effecting the sulfonation of at least a portion of said aromatic hydrocarbonaceous compounds, and thereby forming a sulfonation zone effluent stream which comprises said paraffinic compounds, water-soluble sulfonic acids and oil-soluble sulfonic acids; separating water-soluble sulfonic acids from the sulfonation zone effluent stream by decantation; admixing a first hydrocarbon stream comprising light hydrocarbons having boiling points between 200° and 400° F. with the remaining second portion of the sulfonation zone effluent stream and separating the resultant admixture by a second decantation into a denser phase comprising water-soluble sulfonic acids and a less dense phase comprising oil-soluble sulfonic acids, said light hydrocarbons and said paraffinic hydrocarbons having a molecular weight between about 250 and 450; passing a stream of the less dense phase produced in the second decantation through a saponification zone maintained at saponification conditions including the presence of an aqueous solution of a basic chemical and thereby forming a saponification zone effluent stream comprising said light hydrocarbons, said paraffinic hydrocarbons and oil-soluble petroleum sulfonates; extracting the oil-soluble sulfonates from the saponification zone effluent stream by contacting the saponification zone effluent stream with an aqueous solution of an alkyl alcohol and thereby forming an extract stream comprising oil-soluble sulfonates and a raffinate stream comprising said light hydrocarbons and said paraffinic hydrocarbon; recovering as a product the oil-soluble sulfonates from the extract stream; fractionating the raffinate stream in a fractionation zone maintained at fractionation conditions into a light fraction comprising said light hydrocarbons and a heavy fraction comprising said paraffin hydrocarbons; admixing the light fraction with the remaining second portion of the sulfonation zone effluent as at least a portion of the previously referred to first hydrocarbon stream; passing the heavy fraction through a reforming zone operated at reforming conditions effective to convert at least a portion of said paraffinic hydrocarbons into aromatic hydrocarbons having a molecular weight between 250 and about 400, and thereby forming a reforming zone effluent stream; and passing the reforming zone effluent stream into the sulfonation zone as the previously referred to recycle stream.

I claim as my invention:

1. A process for the production of petroleum sulfonates useful in crude oil production which comprises the steps of:
   (a) passing a feed stream comprising a mixture of aromatic and paraffinic hydrocarbonaceous compounds having a molecular weight between about 250 and about 450, $SO_3$, and a hereinafter specified recycle stream into a sulfonation zone maintained at sulfonation conditions and effecting the sulfonation of at least a portion of said aromatic hydrocarbonaceous compounds, and thereby forming a sulfonation zone effluent stream which comprises said paraffinic compounds, water-soluble sulfonic acids and oil-soluble sulfonic acids;
   (b) separating water-soluble sulfonic acids from the sulfonation zone effluent stream by decantation;
   (c) admixing a first hydrocarbon stream comprising light hydrocarbons having boiling points between 200° and 400° F. with the remaining second portion of the sulfonation zone effluent stream and separating the resultant admixture by a second decantation into a denser phase comprising water-soluble sulfonic acids and a less dense phase comprising oil-soluble sulfonic acids, said light hydrocarbons and said paraffinic hydrocarbons having a molecular weight between about 250 and 450;
   (d) passing a stream of the less dense phase produced in the second decantation through a saponification zone maintained at saponification conditions including the presence of an aqueous solution of a basic chemical and thereby forming a saponification zone effluent stream comprising said light hydrocarbons, said paraffinic hydrocarbons and oil-soluble petroleum sulfonates;
   (e) extracting the oil-soluble sulfonates from the saponification zone effluent stream by contacting the saponification zone effluent stream with an aqueous solution of an alkyl alcohol and thereby forming an extract stream comprising oil-soluble sulfonates and a raffinate stream comprising said light hydrocabons and said paraffinic hydrocarbon;
   (f) recovering as a product the oil-soluble sulfonates from the extract stream;
   (g) fractionating the raffinate stream in a fractionation zone maintained at fractionation conditions into a light fraction comprising said light hydrocarbons and a heavy fraction comprising said paraffin hydrocarbons;
   (h) admixing the light fraction with the second portion of the sulfonation zone effluent as at least a portion of the first hydrocarbon stream of step (c);
   (i) passing the heavy fraction through a reforming zone operated at reforming conditions effective to convert at least a portion of said paraffinic hydrocarbons into aromatic hydrocarbons having a molecular weight between 250 and about 400, and thereby forming a reforming zone effluent stream; and,
   (j) passing the reforming zone effluent stream into the sulfonation zone as the recycle stream of step (a).

2. The process of claim 1 further characterized in that the feed stream is a gas oil.

3. The process of claim 2 further characterized in that the feed stream contains less than 25 mole % aromatics.

4. The process of claim 2 further characterized in that the first hydrocarbon stream is a naphtha.

5. The process of claim 2 further characterized in that the reforming zone comprises a stripping column operated at conditions effective to produce a reforming zone effluent stream which contains substantially no hydrocarbons having a molecular weight less than about 250.

6. The process of claim 5 further characterized in that the feed stream is a vacuum gas oil.

* * * * *